United States Patent
Kirsch et al.

(10) Patent No.: US 6,387,647 B1
(45) Date of Patent: May 14, 2002

(54) CYTOCHROME P-450 REDUCTASE SCREEN FOR ERGOSTEROL BIOSYNTHESIS INHIBITORS

(75) Inventors: Donald Richard Kirsch, Princeton; Margaret Hsien-Fen Kuh Lai, East Brunswick, both of NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/523,302

(22) Filed: Sep. 5, 1995

Related U.S. Application Data

(63) Continuation of application No. 08/066,893, filed on May 25, 1993, now abandoned.

(51) Int. Cl.$^7$ ............ C12Q 1/26; C12P 21/06; C12N 9/02; C12N 1/14
(52) U.S. Cl. ............ 435/25; 435/69.1; 435/189; 435/254.1; 435/254.11
(58) Field of Search .......... 435/25, 69.1, 189, 435/254.1, 254.11, 254.2, 254.21, 255.1, 255.2

(56) References Cited

PUBLICATIONS

Ausubel, F. M. et al, Current Protocols in Molecular Biology, John Wiley, New York, 1989, Unit, 13.10.*
Hata S. et al., Two Species of Cytochrome P450 Involved in Ergosterol Biosynthesis of Yeast, Biochem. Biophys. Res. Communication, 1983, 116, 162–166.*
Garber R. F., Ikeura R. et al, Growth Inhibition of Yeast by Compactin (ML__236__B) Analogues, J. Antibiotics, 1988, 41, 1148–1150.*
Kalb V. et al, Primary Structure of the P450 Lanosterol Demethylase Gene from Sacharomyces cerevisiae, DNA, 1987, vol. 6, 526–537.*
Kalb V. et al, Isolation of Cytochrome P450 Structural Gene form Sacharomyces Cerevisiae, Gene, 1986, 45, 237–245.*
Koeller W., et al, Plant Disease, Fungal Resistance to Sterol Biosynthesis Inhibitors: A New Challenge, 1987, 71, 1066–1074.*
McCommon M. et al. Sterol methylation in Sacharomyces Cerevisiae, Journal of Bacteriology, 1984, 157:475–483.*
Rothstein R. J. One–Step Gene Disruption in Yeast, Methods in Enzymology, 1983, 101, 202–211.*
Turi T. G. et al, Multiple Regulatory Elements Control Expression of the Gne encoding the Sacharomyces cerevisiae Cytochrome P450, Lanosterol 14 alpha–Demethylase, (ERG11), J. Biol. Chem. (1992), 267, 2046–2056.*
Yabusaki Y. et al, Primary Structure of Schaccharomyces cerevisiae NADPH–Cytochrome P450 Reductase Deduced from Nucleotide Sequence of its Cloned Gene, J. Biochem. 1988, 103, 1004–1010.*

* cited by examiner

*Primary Examiner*—Ponnathapu Murthy
*Assistant Examiner*—Malgorzata A. Walicka
(74) *Attorney, Agent, or Firm*—Finnegan, Henderson, Farabow, Garrett & Dunner.

(57) ABSTRACT

A method for screening for potential fungicides identifies biochemical or chemical agents that inhibit the formation of the fungal sterol ergosterol by inhibiting cytochrome P450 reductase or reductase related enzymes or proteins involved in its biosynthesis. Test samples are incubated in two yeast strain cultures, and the extent of growth inhibition is compared between them. One culture is supersensitive to cytochrome P450 reductase inhibitors; the yeast strain typically contains a disrupted or deleted cytochrome P450 reductase gene. The other culture is less sensitive to the compounds, typically exhibiting enhanced permeability such as that observed in erg6 mutants. In preferred embodiments, a known cytochrome P450 reductase related electron-transfer protein inhibitor such as keto-conazole, miconazole, dinaconazole or econazole is employed as a positive control. Preferred embodiments employ solidified media, and test samples are applied to disks or wells. Actives are identified by the production of a zone differential of approximately 8 mm or greater on the yeast culture lawns.

17 Claims, No Drawings

CYTOCHROME P-450 REDUCTASE SCREEN FOR ERGOSTEROL BIOSYNTHESIS INHIBITORS

This is a continuation of application(s) Ser. No. 08-066,893 filed on May 25, 1993, now abandoned.

TECHNICAL FIELD OF THE INVENTION

This invention relates to a screening method for the identification of potential fungicides, based upon use of yeast strains defective in ergosterol biosynthesis.

BACKGROUND OF THE INVENTION

Ergosterol is the principal membrane sterol of fungi. It is structurally similar to its animal counterpart, cholesterol, except that ergosterol has a methyl group and two double bonds not present in cholesterol. In yeast, ergosterol affects membrane fluidity and permeability and plays an essential role in the yeast cell cycle. Yeast cells can take up cholesterol and decrease their requirement for ergosterol to very low levels, but cholesterol alone cannot completely substitute for ergosterol (Gaber, R. F., et al., *Mol. Cell. Biol.* 9: 3447–3456 (1989)).

Though sterol biosynthesis in different organisms have many common steps, the biosynthesis of ergosterol involves steps distinct from cholesterol biosynthesis. These occur after ring formation from squalene, in the transformation of lanosterol to other sterols. One such step is sterol methylation at position 24 in the ergosterol biosynthetic pathway. The enzyme S-adenosylmethionine:$\Delta$24-sterol-C-methyl transferase is responsible for the alkylation. The ERG6 gene encoding this enzyme has been cloned and found to be not essential for growth, but erg6 mutants lacked normal membrane function (Gaber, et al., cited above, and McCammon, M. T., et al., *J. Bact.* 157: 475–483 (1984)).

Another enzyme unique to ergosterol biosynthesis is sterol $\Delta$22 desaturase, which catalyzes the desaturation of ergosta-5,7-dien-3-beta-ol, forming a double bond in ergosterol between carbons at positions 22 and 23 that are not present in cholesterol. This appears to be catalyzed by a cytochrome P450 (Hata, S., et al., *Biochem. Biophys. Res. Com.* 116: 162–166 (1983)).

The term "cytochrome P450" is a trivial name for a class of cytochromes that includes a number of heme proteins that have a characteristic absorption maximum at 450 nm when combined with Co in the reduced state ('P' denotes pigment; hence, the name). These cytochromes occur in many animal tissues, plants and microorganisms and catalyze the monooxygenation of a vast variety of hydrophobic substances including lipophilic endogenous compounds and xenobiotics, serving as oxygenating catalysts in the presence of one or more electron-transfer proteins or redox enzymes. These cytochromes act in concert with a reductase, a flavoprotein that serves as an electron-transfer enzyme from NADPH to cytochrome P450.

A second cytochrome P450 implicated in the ergosterol biosynthetic pathway has a counterpart in cholesterol biosynthesis. This is lanosterol 14-$\alpha$-demethylase, which in yeast catalyzes the oxidative removal of a methyl group at carbon position 14 of lanosterol during ergosterol biosynthesis, and the mammalian orthologue catalyzes the identical reaction in cholesterol biosynthesis (Turi, T. G., and Loper, J. C., *J. Biol. Chem.* 276: 2046–2056 (1992)). Though in higher organisms the diversity of oxidative reactions and broad substrate specificity of the cytochrome P450s are due primarily to the presence of multiple P450s encoded by a gene superfamily that may contain more than 100 genes (Kalb, V. F. et al., *DNA* 6: 529537 (1987)), yeast has been suggested as a model for cytochrome-P450 systems in all eukaryotes (Kalb, V. F., et al., *Gene* 45: 237–245 (1986)). Active enzyme from a mammalian cytochrome P450 clone has been expressed in *Saccharomyces cerevisiae* (Oeda, K., et al., *DNA* 4: 203–210 (1985)).

Cytochrome P450 reductases from a variety of sources have been isolated and compared, and the baker's yeast (*Saccharomyces cerevisiae*) cytochrome P450 reductase gene has been cloned and characterized (Yabusaki, Y., et al., *J. Biochem.* 103: 1004–1010 (1988)). Studies of yeast mutants lacking the cytochrome P450 reductase gene showed that they were viable (Sutter, T. R., and Loper, J. C., *Blochem. Biophys. Res. Com.* 160: 1257–1266 (1989)). However, the cytochrome P450 reductase yeast mutants were 200-fold more sensitive to ketoconazole, an inhibitor of the cytochrome P450 lanosterol 14-$\alpha$-demethylase mentioned above, indicating that the mutants were partially defective. No evidence that these mutants had a second cytochrome P450 reductase gene could be found, so apparently an alternate pathway provides for the functions of this reductase in *S. cerevisiae*.

SUMMARY OF THE INVENTION

It is an object of the invention to provide a screening test for the identification of agents exhibiting potential fungicidal activity for a wide variety of agricultural, medical, and veterinary uses, and for the identification of potential antihypercholesterolemic agents.

It is a further and more specific object of this invention to identify agents that inhibit cytochrome P450 reductase or other enzymes or electron-transfer proteins associated with cytochrome P450 reductase in the ergosterol biosynthetic pathway.

These and other objects are accomplished by the present invention, which provides a method for the identification of agents which inhibit cytochrome P450 reductase involved in ergosterol biosynthesis. The method is a screening test whereby test samples are simultaneously incubated in a culture of a yeast strain supersensitive to inhibitors of cytochrome P450 reductase enzymes or electron-transfer proteins and a second yeast strain exhibiting less sensitivity to these compounds. Agents that are positive in the test inhibit growth more in the supersensitive strain than in the less sensitive strain.

In the practice of this invention's method for screening for the presence or absence of inhibition of cytochrome P450 reductase or cytochrome P450 reductase related enzymes or electron-transfer proteins (cytochrome P450s) by a test sample, the test sample is added to a culture or culture area having a *Saccharomyces cerevisiae* strain having a disrupted cytochrome P450 reductase gene. At the same time, the test sample is added to a control culture or culture area having a *Saccharomyces cerevisiae* strain exhibiting enhanced membrane permeability. The cultures are incubated with the test sample for such time under such conditions sufficient to observe yeast cell growth, ordinarily monitored in corresponding cultures or culture areas of the strains containing no test sample. The extent of inhibition of growth in the culture or culture area containing the cytochrome P450 reductase mutant is then compared with the extent of inhibition in the culture or culture area containing the strain having enhanced membrane permeability. The presence of inhibition of-cytochrome P450 reductase or cytochrome P450 reductase related enzymes or electron-transfer proteins is determined by observation of whether culture growth inhibition in the reductase mutant exceeds that in the permeable mutant.

In a preferred screening test, a *Saccharomyces cerevisiae* strain having a disrupted cytochrome P450 reductase gene is grown in culture in the presence of test samples. At the same time, a *S. cerevisiae* strain having an erg6 mutation is grown in culture with the same test samples. Potentially active agents are identified by the observation of enhanced inhibition of the cytochrome P450 reductase disrupted strain over the erg6 strain. A positive control is employed to assist in the identification of potential agents. In these embodiments, a known inhibitor of cytochrome P450 is used, such as, for example, the lanosterol 14-α-demethylase inhibitors ketoconazole, miconazole, dinaconazole or econazole. Controls are added to both cultures or culture areas, and relative inhibition is compared with that observed with the test samples.

In a particularly preferred embodiment, the cytochrome P450 reductase disrupted strain and the erg 6 yeast strain are grown in a solidified media in a plate or dish, so that test samples and positive controls can be observed visually and simultaneously as regions of the same culture. Actives produce a much larger zone (~≧8 mm) around test samples grown in a lawn of the reductase deleted strain than in a lawn of the erg6 strain.

Detailed Description of the Invention

This screening method is based upon the finding that a pair of *Saccharomyces cerevisiae* strains exhibiting defective ergosterol biosynthesis are useful for a screening assay for inhibitors of cytochrome P450 reductase, and cytochrome P450 reductase related enzymes or electron-transfer proteins (i.e., cytochrome P450 species). One strain is supersensitive to inhibitors of cytochrome P450 species and the second strain exhibits less sensitivity to these compounds.

*Saccharomyces cerevisiae* strains supersensitive to inhibitors of cytochrome P450 species include strains having a disrupted or deleted cytochrome P450 reductase gene. Baker's yeast is easily manipulated genetically, and, as has been discussed, the NADPH-cytochrome P450 reductase yeast gene has been well studied, with the primary structure known (Yabusaki, Y., et al., cited above). Disruption of the gene can be effected using published procedures (summarized in Ausubel, F. M., et al., eds., *Current Protocols in Molecular Biology*, John Wiley, New York, 1989, Unit 13.10) including the popular one-step disruption, wherein a cloned DNA fragment containing the gene is digested with a restriction enzyme that cleaves the gene sequence, and another DNA fragment is cloned into the cleaved gene (Rothstein, R. J., *Methods in Enzymology* 101: 202–211 (1983)); integrative disruption, wherein an internal fragment of a cloned gene is introduced into the chromosome on an integrating plasmid, generating gene duplication of copies that are not intact so that a deletion in the chromosomal copy of the gene is generated; and clone transplacement, a rearrangement and replacement of DNA fragments accomplished by introducing a mutated, usually marked, gene on a plasmid, integrating it, allowing the plasmid to be evicted, and then screening for the mutant phenotype.

Sutter and Loper, cited above, for example, prepared mutants having disrupted cytochrome P450 reductase genes by replacing a 700 base pair cytochrome P450 reductase gene fragment with a 3.2 kilobase pair LEU2-containing fragment isolated from a plasmid to yield leucine prototrophs denoted in the paper as TSY11-6C and TSY21 which contained disrupted cytochrome P450 reductase genes. Both strains were sensitive to ketoconazole. Another strain containing a disrupted cytochrome P450 reductase gene that is useful in this invention, denoted DCX45(pML82)-1B, is prepared by cloning the gene and disrupting it by insertion of the LEU2 yeast gene as described by Rothstein, cited above, and illustrated in Example 1 below.

A second strain of *Saccharomyces cerevisiae* that exhibits less sensitivity to compounds that inhibit cyto-chrome P450 is employed in the method of this invention. Strains exhibiting enhanced membrane permeability are preferred such as erg6 mutants described by Gaber, et al., and McCammon, M. T., et al., cited above, erg2, or erg5 mutants. As has been discussed, ERG6 is the putative structural gene for the enzyme that catalyzes the methylation at the C-24 position of sterol in the biosynthesis of ergosterol in yeast. Mutant erg6 strains have disrupted, deactivated or deleted ERG6 genes. Gaber, et al., prepared two erg6 mutants and found the gene to be not essential for growth, but the strains exhibited hypersensitivity to cycloheximide, resistance to nystatin, decreased mating frequency, decreased transformation freguency and decreased tryptophan uptake. One strain was a deletion-substitution mutant generated by deleting a 400 base pair in ERG6 and inserting a 1.9 kilobase pair fragment containing the LEU2 gene. A second strain was prepared by simply removing at least 90% (~2.9 kilobases) of the ERG6 gene. Any erg2, erg5 or erg6 mutant can be employed in the method of this invention. In one embodiment, erg6 mutant strain STX429–2A obtained from the Yeast Genetics Stock Center is employed.

In the practice of this invention's method, the test sample is added to a culture or culture area of a *Saccharomyces cerevisiae* strain supersensitive to inhibitors of cytochrome P450 such as a strain having a disrupted cytochrome P450 reductase gene. At the same time, the test sample is added to a culture or culture area having a *Saccharomyces cerevisiae* strain exhibiting enhanced membrane permeability such as an erg6 mutant. The two cultures are incubated with the test samples together for such time under such conditions sufficient to observe yeast cell growth in corresponding cultures or culture areas of the strains containing no test sample. The extent of inhibition of growth in the culture or culture areas of the two strains are then compared. The presence of inhibition of cytochrome P450 or cytochrome P450 reductase is determined by observation of enhanced culture growth inhibition in the supersensitive strain.

Any type of solidified or liquid media that will support growth and reproduction of the *S. cerevisiae* strains may be employed as cultures in the method of this invention. Numerous yeast media are known to the skilled artisan, and an advantage of the invention is that baker's yeast is relatively easy to grow. Typical media are yeast extract, peptone and dextrose (YEPD) or yeast extract and dextrose (YED) media; yeast basal growth media (YBGM) containing glucose, vitamins, minerals, and water; yeast extract, peptone, and adenine sulfate (YPA) media; yeast mannitol (YM) media and YM plus glucose; synthetic dextrose (SD) media containing dextrose, a nitrogen base, water, and, optionally amino acids, adenine sulfate and uracil; and the like.

Where liquid cultures are employed, differences in growth are generally determined by observing and comparing turbidity; for this purpose, optical density (OD) readings at 550 to 650 nm are made and compared. Preferred media, however, are solidified by adding agar or gelatin forming cultures in plates or dishes. Agar is especially preferred. In these embodiments, differential growth is observed visually.

In a preferred screening test, a *Saccharomyces cerevisiae* strain having a disrupted cytochrome P450 reductase gene such as TSY11-6C, TSY21 or DCX45(pML82)-1B is grown in culture in the presence of test samples. At the same time, a *S. cerevisiae* strain having an erg6 mutant such as STX429-2A is grown in culture with the same test samples.

Potentially active agents are identified by the observation of enhanced inhibition of the cytochrome P450 reductase disrupted strain over the erg6 strain.

In preferred embodiments, a positive control is employed to assist in the identification of potential agents. In these embodiments, a known inhibitor of a cytochrome P450 reductase related electron-transfer protein is employed. For example, a known lanosterol 14-α-demethylase inhibitor such as ketoconazole, miconazole, dinaconazole, or econazole is useful as a control. Positive controls are added to cultures or culture areas of both *S. cerevisiae* strains, and the control effects on culture growth are compared to the cultures or culture areas with the test samples.

As mentioned above, particularly preferred embodiments employ solidified media, so that test samples and positive controls are observed visually and simultaneously as regions of the same culture. Samples or controls are introduced on a disk or in a well of the plate. Inhibition is observed visually as measurable zones around disks or wells in the lawn of growth in the plate or dish. Actives produce a much larger zone ($\sim \geq 8$ mm) around test samples grown in a lawn of the reductase disrupted strain than in a lawn of the erg6 strain.

A distinct advantage of the invention is its speed and simplicity. The protocol is extremely simple. Many samples are readily analyzed in a short time, providing new potential sterol biosynthesis inhibitors that can be employed in the arsenal against undesirable fungi, some of which are resistant to currently known fungicides (including sterol biosynthesis inhibitors, see Koeller, W., and Scheinpflug, H., *Plant Disease* 71: 1066–1074 (1987)), and that interfere with pathogen but not host metabolism.

It is another advantage of the invention that it is sensitive, and only small amounts of biochemical or chemical agents are required for the test. In a standard assay of the invention, for example, which employs solidified media in a plate, as little as 20 µg of a biochemical or chemical test sample or control are be applied to a disk or in a well.

The assay is a moderate positive rate assay (~0.04%), so that secondary tests may be considered to prioritize actives found using the screen. Standard in vitro and in vivo fungicide discovery screens can be employed for this. In vitro screens test samples for their ability to inhibit the growth of selected phytopathogenic fungi cultured in nutrient agar. These include but are not limited to fungi causing wheat eyespot (*Pseudocercosporella herpotrichoides*), rice s heath blight (*Rhizoctonia solani*) and damping off (*Fusarium oxysporum*), which all synthesize ergosterol. In in vivo screens, a variety of phytopathogenic fungi are used to infect plants treated with test compounds. Active compounds block or reduce the appearance of disease symptoms. A number of model plant infections can be employed and include ergosterol-producing fungi causing apple scab (*Venturia inaequalis*), pepper botrytis (Botrytis cincerea), rice blast (*Pyricularia oryzae*), sugar beet cercospora (*Cercospora beticola*), tomato early blight (*Alternaria solani*), wheat leaf rust (*Puccinia recondita tritici*), and wheat powdery mildew (*Eerysiphe graminis tritici*).

The following examples are p resented to further illustrate and explain the present invention and should not be taken as limiting in any regard.

EXAMPLE 1

This example illustrates the preparation of a *S. cerevisiae* strain containing a disrupted cytochrome P450 reductase gene useful for the method of this invention. This strain, denoted DCX45(pML82)-1B, is constructed by independent cloning and disruption of the cytochrome P450 reductase gene by insertion of the yeast LEU2 into it.

λ-gtll yeast genomic library (obtained from Clontech) is probed with two sequences synthesized by New England Biolabs, Inc. corresponding to basepairs 271 to 300 (GTGATGTGCGCAGATGTTGAGAACTACGAC) SEQ ID NO: 1 and basepairs 1951 to 1980 (GCCAAGGGTGTGTCAACCGCATTGGTTGGC) SEQ ID NO: 2 of the cytochrome P450 reductase gene published by Yabusaki, et al., cited above.

$^{32}$P-adenosine triphosphate (ATP) obtained from NEN® Research Products is used to randomly label the probes using a polynucleotide kinase. The reaction mixture comprising 1 µl DNA containing 100 ng to 1 µg material made up in water, 1.5 µl polynucleotide kinase (10,000 U/ml), 2 µl 10X kinase buffer (0.5 M Tris, pH 7.6, 0.1 M $MgCl_2$, 50 mM DTT, 1 mM spermidine, 1 mM EDTA), 6 µl $^{32}$P-ATP, and 9.5 µl water, is incubated 1 hour at 37° C. and separated on a G50 column (in water) in a 10 ml disposable pipet.

Library screenings employ duplicate nitrocellulose filters. Prior to prehybridization, filters are floated on 6×SSC (standard saline citrate) until wetted and prewashed at 42° C. for for 1 hour in a 50 mM pH 8 Tris-HCl buffer, 1 M NaCl, 1 mM EDTA, 0.1% SDS solution. Prehybridizations are at 42° C. for 4 hours in a solution containing 5×Denhardt's solution, 5×SSC, 0.1% SDS, and 100 µg/ml denatured salmon sperm DNA. Hybridizations are carried out overnight at 37° C. in 20 ml (for 15 filters) prehybridization solution with 500 µl probes, and then washed twice with 5×SSC at 37° C. (20 minutes per wash). Hybridizations are verified by exposing x-ray films overnight.

Screening is continued by plating out selected phages, plaque picking, reprobing picked plaques, verifying the probing results, replating, and reprobing several times using the procedure outlined above to identify phage DNA positive to both probes. Restriction mapping using BamHI, EcoRI, KpnI, and SstI (SacI) suggests that the phage contain the cytochrome P450 reductase gene.

The cloned gene is then disrupted by digesting with a restriction enzyme that cleaves within the locus, and inserting a DNA fragment coding for yeast gene LEU2 as a selectable marker into the cleaved gene. The phage containing reductase gene is cut with KpnI and inserted into KpnI site of pUC18 to form pML81. LEU2 is removed from YEp13 as a 3.0 KB BglII fragment and inserted into pML81 (pUC18 with KpnI fragment of P450 reductase gene) at the BamHI site. DNAs are ligated with T4 ligase in 25 µl 5×ligase buffer and 99 µl water to obtain plasmids containing the disrupted gene.

The ligation mixture is transformed into *E. coli* strain RR1. DNA (pML82) is isolated from the bacterial transformant and identified to contain the disrupted gene. pML82 is digested with restriction enzymes SstI and BamHI, precipitated by ethanol in the presence of 0.2 M NaCl and transformed into yeast strain DCX45 having the genotype MATa/α, leu2-2,112/leu2,112,his3-11,15/HIS3, HIS4/his4-519, URA3/ura3, TRPl/trpl to obtain the Leu$^+$ heterozygote. DNAs from yeast transformants are isolated and shown to contain disrupted gene by Southern analysis. The NEN Gene Screen Plus® system is employed to ascertain DNA transferred, and hybridization is carried out to ascertain that insertion occurs in the correct place.

This strain is sporulated and tetrads dissected and is grown on 5 media to identify nutritional markers in addition to LEU2: (1) synthetic dextrose media (SD)+leucine+ histidine+uracil+tryptophan; (2) SD+leucine+histidine+ uracil; (3) SD+leucine +histidine+tryptophan; (4) SD+leucine+uracil+tryptophan; and (5) SD+histidine+ uracil+tryptophan. Spores exhibiting LEU⁺ and leu⁻ are then plated out on complete yeast media YEPD, and disks containing the known reductase inhibitors ketoconazole, econazole, and dinaconazole are placed on the media with the cultures. Cultures exhibiting LEU⁺ are more sensitive to 14-α-demethylase inhibitors. The strain most sensitive to 14-α-demethylase inhibitors is denoted DCX45(pML82)-1B.

The strain shows supersensitivity to ketoconazole and other lanosterol 14-α-demethylase inhibitors. However, the strain unexpectedly shows increased sensitivity to a number of antifungals such as cycloheximide and cerulenin having sites of action unrelated to sterol biosynthesis. This may be due to alterations in membrane permeability caused by the mutation.

EXAMPLE 2

In order to determine the efficacy of the cytochrome P450 reductase screen of this invention, a large number of compounds are tested using the method of this invention, including known ergosterol biosynthesis inhibitors in a panel of fungicides, antibiotics and herbicides selected to represent diverse mechanisms of action.

Liquid yeast extract, peptone and dextrose (YEPD) media is first prepared by mixing the following ingredients obtained from Difco

| Yeast Extract | 10 gm |
| Peptone | 20 gm |
| Dextrose | 20 gm |
| Distilled water | 1000 ml | and autoclaving at 20 lbs for 15 min. Solidified YEPD media is prepared using the above ingredients, except that Agar (Difco) 20 gm is added prior to autoclaving.

Overnight cultures of S. cerevisiae strain DCX45-(pML82)-1B from Example 1 above and strain STX429-2A obtained from the Yeast Genetics Stock Center are grown in liquid YEPD media shaken at 30° C. to an $OD_{600}$ of ~5 or greater.

Test media are prepared by combining separately 0.5 parts STX429-2A inoculum to 100 parts of warm YEPD agar media and 2 parts of DCX45(pML82)-1B to 100 parts of warm YEPD agar media. Plates for each culture are poured. Test samples are prepared on disks in duplicate, and each is placed on a STX429-2A plate and a DCX45(pML82)-1B plate, testing 20 μg of test sample per disk. A ¼" disk containing 10 μg of dinaconazole is used as a positive control on each plate.

The plates are incubated at 30° C. for two days and then examined to compare activity on the two strains. Actives produce a larger zone on the DCX45(pML82)-1B plate than on the STX429-2A plate. Only compounds producing a differential of approximately 8 mm or more are scored as active.

Using this procedure, the panel of standard fungicides, antibiotics and herbicides listed in Table I are tested. In the panel, the only compounds active using the cytochrome P450 reductase screen are the known lanosterol 14-α-demethylase inhibitors ketoconazole, miconazole, dinaconazole and econazole.

TABLE I

STANDARD FUNGICIDE PANEL

| Compound | Target |
| --- | --- |
| amphotericin B | plasma membrane (polyene) |
| cerulenin | fatty acid biosynthesis |
| haloprogin | respiration |
| ketoconazole | ergosterol biosynthesis (lanosterol 14α-demethylase) |
| miconazole | ergosterol biosynthesis (lanosterol 14α-demethylase) |
| dinaconazole | ergosterol biosynthesis (lanosterol 14α-demethylase) |
| econazole | ergosterol biosynthesis (lanosterol 14α-demethylase) |
| fenarimole | ergosterol biosynthesis (sterol Δ14 reductase) |
| tridemorph | ergosterol biosynthesis (sterol Δ14 reductase) |
| tolnaftate | ergosterol biosynthesis (squalene monooxygenase) |
| U18666A | ergosterol biosynthesis (squalene cyclase) |
| cycloheximide | protein biosynthesis |
| polyoxin D | chitin biosynthesis (cell wall) |
| nikkomycin | chitin biosynthesis (cell wall) |
| nocodazole | microtubule |
| benomyl | microtubule |
| maneb | multi-target |
| metalaxyl | rRNA biosynthesis |
| vinclozolin | lipid peroxidation |
| kanamycin | mitochondria |
| tunicazuycin | glycoprotein biosynthesis |
| carboxin | succinate dehydrogenase |
| cyanobutarate | microtubule (plant) |
| antimycin | respiration |
| 5-fluoro-cytosine | nucleotide metabolism |
| glyphosate | herbicide (aromatic amino acid biosynthesis) |
| phosphinothricin | herbicide (glutamine biosynthesis) |
| aminotriazole | herbicide (histidine biosynthesis) |
| sulfometuron methyl | herbicide (branched chain amio acid biosynthesis) |
| pendimethalin | herbicide (microtubule) |

The imidazole sensitivity of these compounds in the strains is as follows:

| | Limit of Detection | | |
| --- | --- | --- | --- |
| strain | ketoconazole | econazole | diniconazole |
| STX429-2A (erg 6) | 100 ng | 50 ng | 50 ng |
| DCX45 (pML82)-1B | 5 ng | 2 ng | 2 ng |

The panel of varied antibiotic types listed in Table II are tested using the cytochrome P450 reductase assay of this invention. All compounds are tested by disk diffusion assay at a rate of 20 μg/disk. Of the compounds in the panel, only gliotoxin is positive. Since gliotoxin is not a known inhibitor of ergosterol biosynthesis,>this demonstrates that the assay is not completely specific.

TABLE II

STANDARD ANTIBIOTIC PANEL

| pimaricin (tennecetin) | streptogramin ("type") |
| monazomycin | nystatin |
| aspartocin | bacitracin |

TABLE II-continued

STANDARD ANTIBIOTIC PANEL

| | |
|---|---|
| clavacin | citrinin |
| avoparcin | isoquinocycline |
| neutramycin | A1531 |
| leucomycin | AO341β |
| angustmycin A & C | gliotoxin |
| gibberellic acid | puromycin |
| puromycin aminonucleoside | BM123α |
| etamycin | mocimycin |
| neomycin | viomycin |
| netropsin | lincomycin |
| picromycin | A9537 |
| AN272α | levomycin |
| AM374 | antiprozoin |
| BL580 zeta | actithiazic acid |
| hamycin | carbomycin |
| frenolicin | fusarinic acid |
| BL580α | tylosin |
| declomycin | tetrahydro spiramycin |
| usnic acid | geldanamycin |
| Z122OA | BM782ε |
| BO2964 complex | choramphenicol |
| A8363 | actinomycin |
| BM123γ | AD97 |
| phenazine α | paromomycin |
| streptomycin | A4825 |
| alazopeptin | nucleocidin |
| nonactin | valinomycin |
| C19004 complex | avilamycin |
| V214W | V214X |
| vancomycin | ristocetin |
| relomycin | CO8078α |
| blasticidin S | 4-dedimethylamino-4-methyla-mino-anhydrotetracycline |

Eleven actives are obtained in a screen of almost 7000 synthetic compounds using the assay. Six actives are observed in a screen of 16,861 fermentation samples. Thus, the assay has a moderate positive activity rate (~0.04%).

The assay is further tested using compactin, a specific potent inhibitor of 3-hydroxy-3-methylglutaryl (HMG)-CoA reductase, the major rate-limiting enzyme in the biosynthesis of isoprenoid compounds (Ikeura, R., et al., *J. Antibiotics* 41: 1148–1150 (1988)). In the assay of this invention, lactonized mevinolin (monacolin K, extracted from commercially obtained mevacor) produces no response when used at high levels (20 μg).

The following *Saccharomyces cerevisiae* strains have been deposited at American Type Culture Collection (ATCC) (Manassas, Va. 20110-2209 USA). *Saccharomyces cerevisiae* strain DCX45(pML82)-1B (ATCC Patent Deposit No. PTA-3406) and *Saccharomyces cerevisiae* strain STX429-2A (ATCC Patent Deposit No. PTA-3407) were deposited at ATCC on May 24, 2001. *Saccharomyces cerevisiae* strain TSY21 (ATCC Patent Deposit No. PTA-3408) was deposited at ATCC on May 25, 2001.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are meant to cover the claimed components and steps in any sequence which is effective to meet the objectives there intended, unless the context specifically indicates the contrary.

BIBLIOGRAPHY

Ausubel, F. M., et al., eds., *Current Protocols in Molecular Biology*, John Wiley, New York, 1989, Unit 13.10.

Gaber, R. F., et al., *Mol. Cell. Biol.* 9: 3447–3456 (1989).

Hata, S., et al., *Biochem. Biophys. Res. Com.* 116: 162–166 (1983).

Ikeura, R., et al., *J. Antibiotics* 41: 1148–1150 (1988).

Kalb, V. F. et al., *DNA* 6: 529–537 (1987).

Kalb, V. F., et al., *Gene* 45: 237–245 (1986).

Koeller, W., and Scheinpflug, H., *Plant Disease* 71: 1066–1074 (1987).

McCammon, M. T., et al., *J. Bact.* 157: 475–483 (1984).

Rothstein, R. J., *Methods in Enzymology* 101: 202–211 (1983).

Sutter, T. R., and Loper, J. C., *Biochem. Biophys. Res. Com.* 160: 1257–1266 (1989).

Turi, T. G., and Loper, J. C., *J. Biol. Chem.* 267: 2046–2056 (1992).

Yabusaki, Y., et al., *J. Biochem.* 103: 1004–1010 (1988).

What is claimed is:

1. A method for screening for the presence or absence of inhibition of cytochrome P450 or cytochrome P450 related enzymes or electron-transfer proteins by a test sample which comprises:
   (a) adding said test sample to a culture of a *Saccharomyces cerevisiae* strain having a disrupted cytochrome P450 reductase gene; wherein said cytochrome P450 reductase gene is involved in the ergosterol synthetic pathway
   (b) adding said test sample to a second culture of a *Saccharomyces cerevisiae* strain having an erg6 mutation;
   (c) incubating said test samples in said cultures for such time under such conditions sufficient to observe yeast cell growth in corresponding cultures containing no test sample;
   (d) comparing the extent of growth inhibition in the culture containing the disrupted P450 reductase gene with the extent of growth inhibition in the culture containing the erg6 mutant; and
   (e) determining the presence of said cytochrome P450 or cytochrome P450 related enzymes or electron-transfer proteins inhibition by observation of whether growth inhibition in the disrupted reductase growth culture exceeds growth inhibition in the erg6 culture.

2. A method according to claim 1 further comprising the step of providing a control by adding a known inhibitor of a cytochrome P450 or related electron transfer protein or enzyme to both *S. cerevisiae* strains prior to incubation.

3. A method according to claim 2 wherein said inhibitor is a lanosterol 14-α-demethylase inhibitor selected from the group consisting of ketoconazole, miconazole, dinaconazole, and econazole.

4. A method according to claim 3 wherein said inhibitor is dinaconazole.

5. A method according to claim 1 wherein said *Saccharomyces cerevisiae* strain having an erg6 mutation is strain STX429-2A obtained from the Yeast Genetics Stock Center.

6. A method according to claim 5 wherein said *Saccharomyces cerevisiae* strain having a disrupted cytochrome P450 reductase gene is selected from the group consisting of strain DCX45(pML82)-1B, strain TSY11-6C, and strain TSY21.

7. A method according to claim 6 wherein said *Saccharomyces cerevisiae* strain is strain DCX45(pML82)-1B.

8. A method according to claim 1 wherein said cultures containing test samples are solidified cultures and test samples are added to the cultures on a disk or in a well.

9. A method according to claim 1 wherein said cultures are liquid cultures.

10. A method for screening for the presence or absence of inhibition of cytochrome P450 or cytochrome P450 related enzymes or electron-transfer proteins by a chemical or biochemical test sample which comprises:

(a) preparing, in a culture plate, a solidified culture of a *Saccharomyces cerevisiae* strain containing a disrupted cytochrome P450 reductase gene; wherein said cytochrome P450 reductase gene is involved in the ergosterol synthetic pathway (b) preparing, in another culture plate, a solidified culture of a *Saccharomyces cerevisiae* strain having an erg6 mutation;

(c) introducing into both said cultures identical chemical or biochemical test samples in a well or on a disk;

(d) introducing into said cultures, in a well or on a disk, a positive control selected from the group consisting of ketoconazole, miconazole, dinaconazole, and enconzole;

(e) incubating said cultures for such time under such conditions sufficient to observe yeast cell growth in the absence of test samples;

(f) comparing the extent of growth in the cultures of both strains in the vicinity of test samples and in the vicinity of the positive control with the extent of growth in the rest of the culture; and (g) determining the presence of inhibition of said cytochrome P450 or related proteins or enzymes by observation of whether growth inhibition in the vicinity of test sample in the disrupted reductase gene culture exceeds inhibition in the erg6 culture.

11. A method according to claim 10 wherein the *Saccharomyces cerevisiae* strain containing a disrupted cytochrome P450 reductase gene is DCX45(pML82)-1B and the *Saccharomyces cerevisiae* strain containing the erg6 mutation is strain STX429-2A.

12. A method according to claim 11 wherein the positive control is dinaconazole.

13. A method according to claim 12 comprising a disk diffusion assay wherein 20 µg test sample and 10 µg positive control are tested per disk or well.

14. A method for screening for the presence or absence of cytochrome P450 or cytochrome P450 reductase inhibition by a test sample which comprises:

(a) adding said sample to a well in, or a disk on, a solidified culture of a *Saccharomyces cerevisiae* strain containing a disrupted cytochrome-P450 reductase gene; wherein said cytochrome P450 reductase gene is involved in the ergosterol synthetic pathway (b) adding said sample to a well in, or a disk on, a solidified culture of a *Saccharomyces cerevisiae* strain having an erg6 mutation;

(c) incubating said cultures for such time under such conditions sufficient to observe yeast cell growth in the absence of test sample;

(d) comparing the extent of growth in the cultures of both strains in the vicinity of test samples; and, (e) determining the presence of inhibition of said cytochrome P450 or cytochrome P450 reductase by observation that growth inhibition in the vicinity of test sample in the disrupted reductase gene culture exceeds inhibition in the erg6 culture by at least about 8 mm.

15. A method according to claim 14 wherein a cytochrome P450 inhibitor is used as a positive control in both cultures.

16. A method according to claim 15 wherein said inhibitor is a lanosterol 14-α-demethylase inhibitor.

17. A method according to claim 16 wherein said inhibitor is dinaconazole.

* * * * *